US00PP34331P2

(12) United States Plant Patent
van SAMBEEK

(10) Patent No.: US PP34,331 P2
(45) Date of Patent: Jun. 14, 2022

(54) ***ERYSIMUM* PLANT NAMED 'DOERYWACI'**

(50) Latin Name: *Erysimum hybrida*
Varietal Denomination: Doerywaci

(71) Applicant: DUMMEN GROUP B.V., De Lier (NL)

(72) Inventor: Ellen van SAMBEEK, Oegstgeest (NL)

(73) Assignee: DUMMEN GROUP B.V., De Lier (NL)

( * ) Notice: Subject to any disclaimer, the term of this patent is extended or adjusted under 35 U.S.C. 154(b) by 0 days.

(21) Appl. No.: 17/499,053

(22) Filed: Oct. 12, 2021

(51) Int. Cl.
*A01H 5/02* (2018.01)
*A01H 6/00* (2018.01)

(52) U.S. Cl.
USPC ..... Plt./263.1
CPC ..... *A01H 6/00* (2018.05)

(58) Field of Classification Search
USPC ..... Plt./263.1
CPC ..... A01H 6/00
See application file for complete search history.

(56) References Cited

PUBLICATIONS

CPVO Application Consultation, UPOV hit on *Erysimum* plant named, 'Doerywaci', QZ PBR 2021/1408, Jun. 1, 2021.*

* cited by examiner

*Primary Examiner* — Anne Marie Grunberg
(74) *Attorney, Agent, or Firm* — C. Anne Whealy

(57) ABSTRACT

A new and distinct cultivar of *Erysimum* plant named 'Doerywaci', characterized by its compact, upright and mounding plant habit; moderately vigorous growth habit; freely branching habit; dense and bushy habit; freely and continuous flowering habit; long flowering period; large light to bright yellow-colored flowers; tolerance to low and high temperatures and good garden performance.

1 Drawing Sheet

Botanical designation: *Erysimum hybrida.*
Cultivar denomination: 'DOERYWACI'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Dümmen Group B.V. of De Lier, The Netherlands on Jun. 1, 2021, application number 2021/1408. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Erysimum* plant, botanically known as *Erysimum hybrida*, commonly referred to as Wallflower and hereinafter referred to by the name 'Doerywaci'.

The new *Erysimum* plant is a product of a planned breeding program conducted by the Inventor in Aalsmeer, The Netherlands. The objective of the breeding program was to develop new compact *Erysimum* plants with numerous large and attractive flowers.

The new *Erysimum* plant originated from a cross-pollination in February, 2017 in Aalsmeer, The Netherlands of a proprietary selection of *Erysimum hybrida* identified as code number ER16-000001-029, not patented, as the female, or seed, parent, with a proprietary selection of *Erysimum hybrida* identified as code number ER16-000001-023, not patented, as the male, or pollen, parent. The new *Erysimum* plant was discovered and selected by the Inventor as a single flowering plant within the progeny of the stated cross-pollination in a controlled greenhouse environment in Aalsmeer, The Netherlands in April, 2018. Asexual reproduction of the new *Erysimum* plant by vegetative terminal cuttings in a controlled greenhouse environment in Aalsmeer, The Netherlands since May, 2018 has shown that the unique features of this new *Erysimum* plant are stable and reproduced true to type in successive generations.

SUMMARY OF THE INVENTION

Plants of the new *Erysimum* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Doerywaci'. These characteristics in combination distinguish 'Doerywaci' as a new and distinct *Erysimum* plant:

1. Compact, upright and mounding plant habit.
2. Moderately vigorous growth habit.
3. Freely branching habit; dense and bushy habit.
4. Freely and continuous flowering habit.
5. Long flowering period.
6. Large light to bright yellow-colored flowers.
7. Tolerant to low and high temperatures and good garden performance.

Plants of the new *Erysimum* differ primarily from plants of the female parent selection in flower color as plants of the new *Erysimum* have light to bright yellow-colored flowers whereas plants of the female parent selection have orange and purple-colored flowers.

Plants of the new *Erysimum* differ primarily from plants of the male parent selection in flower color as plants of the new *Erysimum* have light yellow to bright yellow-colored flowers whereas plants of the male parent selection have pastel yellow and pink-colored flowers.

Plants of the new *Erysimum* can be compared to *Erysimum hybrida* 'Poem Pastel', not patented. In side-by-side comparisons, plants of the new *Erysimum* differ from plants of 'Poem Pastel' in the following characteristics:

1. Plants of the new *Erysimum* are more compact than plants of 'Poem Pastel'.
2. Plants of the new *Erysimum* have larger flowers than plants of 'Poem Pastel'.
3. Flowers of plants of the new *Erysimum* are light to bright yellow in color whereas flowers of plants of 'Poem Pastel' are pastel pink and yellow in color.

BRIEF DESCRIPTION OF THE PHOTOGRAPH

The accompanying colored photograph illustrates the overall appearance of the new *Erysimum* plant showing the colors as true as it is reasonably possible to obtain in colored reproductions of this type. Colors in the photograph may differ slightly from the color values cited in the detailed botanical description which accurately describe the colors of the new *Erysimum* plant. The photograph is a top perspective view of a typical flowering plant of 'Doerywaci' grown in a container.

DETAILED BOTANICAL DESCRIPTION

The aforementioned photographs and following observations and measurements describe plants grown in 17-cm containers in a glass-covered greenhouse in Aalsmeer, The Netherlands and under cultural practices typical of commercial *Erysimum* production. During the production of the plants, average daily temperatures were 21° C. and average night temperatures were 15° C. Plants were 22 weeks old when the photograph and description were taken. In the following description, color references are made to The Royal Horticultural Society Colour Chart, Second Edition, except where general terms of ordinary dictionary significance are used. Measurements were taken on individual plants.

Botanical classification: *Erysimum hybrida* 'Doerywaci'.

Parentage:

*Female, or seed, parent*.—Proprietary selection of *Erysimum hybrida* identified as code number ER16-000001-029, not patented.

*Male, or pollen, parent*.—Proprietary selection of *Erysimum hybrida* identified as code number ER16-000001-023, not patented.

Propagation:

*Type*.—Terminal vegetative cuttings.

*Time to initiate roots, summer*.—About twelve days at temperatures about 26° C.

*Time to initiate roots, winter*.—About 16 days at temperatures about 23° C.

*Time to produce a rooted young plant, summer*.—About 16 days at temperatures about 23° C.

*Time to produce a rooted young plant, winter*.—About 20 days at temperatures about 18° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant form and growth habit*.—Perennial garden or container plant; compact, upright to mounding plant habit; freely branching habit with about 23 lateral branches developing per plant; dense and bushy appearance; moderately vigorous growth habit and moderate growth rate.

*Plant height*.—About 22 cm.

*Plant diameter* (*area of spread*).—About 22 cm.

*Lateral branches*.—Length: About 16 cm. Diameter: About 4 mm. Internode length: About 3 mm. Strength: Strong. Aspect: Upright to about 45° from vertical. Texture and luster: Smooth, glabrous; glossy. Color, developing and developed: Close to 144A.

Leaf description:

*Arrangement*.—Alternate; simple; sessile.

*Length*.—About 7.5 cm.

*Width*.—About 1.5 cm.

*Shape*.—Narrowly oblanceolate with lanceolate tendencies.

*Apex*.—Acute.

*Base*.—Cuneate.

*Margin*.—Entire with some serrations.

*Texture and luster, upper and lower surfaces*.—Sparsely pubescent; semi-glossy.

*Venation pattern*.—Single midvein discernible.

*Color*.—Developing leaves, upper surface: Close to 137A. Developing leaves, lower surface: Close to 138A. Fully developed leaves, upper surface: Close to 137B; venation, close to 144B. Fully developed leaves, lower surface: Close to 138B; venation, close to 138B.

Flower description:

*Flower type and habit*.—Large rounded cruciform flowers arranged in dense racemes; flowers face mostly upright; freely flowering habit, about ten flowers per inflorescence and about 312 flowers developing per plant.

*Natural flowering season*.—Relatively long flowering period; plants flower continuously from spring until autumn in The Netherlands; flowers not persistent.

*Fragrance*.—Moderately fragrant; sweet, pleasant.

*Inflorescence height*.—About 7 cm.

*Inflorescence diameter*.—About 4.5 cm.

*Flower diameter*.—About 2 cm.

*Flower depth* (*height*).—About 1.2 cm.

*Flower buds*.—Length: About 6 mm. Diameter: About 5 mm. Shape: Elliptic. Texture and luster: Smooth, glabrous; matte. Color: Close to 9A.

*Petals*.—Quantity and arrangement: Four petals arranged in a single whorl. Length: About 1 cm. Width: About 1.4 cm. Shape: Roughly spatulate. Apex: Obtuse. Base: Cuneate. Margin: Entire, slightly undulate. Texture and luster, upper and lower surfaces: Smooth, glabrous; matte. Color: When opening, upper and lower surfaces: Close to 12A. Fully opened, upper surface: During development, flowers transition through the following colors, close to 12A, 12C and 12D; venation, similar to lamina colors. Fully opened, lower surface: During development, flowers transition through the following colors, close to 12B, 158B and 158C; venation, similar to lamina colors.

*Sepals*.—Quantity and arrangement: Four sepals arranged in a single whorl; calyx, tubular. Length: About 1 cm. Width: About 3 mm. Shape: Subulate. Apex: Acuminate. Base: Cuneate. Margin: Entire. Texture and luster, upper surface: Smooth, glabrous; matte. Texture and luster, lower surface: Smooth, glabrous; semi-glossy. Color, upper and lower surfaces: Close to 144B.

*Pedicels*.—Length: About 8 mm. Width: About 1 mm. Strength: Flexible. Aspect: About 45° from peduncle axis. Texture and luster: Smooth, glabrous; semi-glossy. Color: Close to 143A.

*Reproductive organs*.—Stamens: Quantity per flower: Six. Filament length: About 9 mm. Filament color: Close to 145C. Anther shape: Elliptic; dorsifixed. Anther size: About 1 mm by 3 mm. Anther color: Close to 145C. Pollen amount: Abundant. Pollen color: Close to 158A. Pistils: Quantity per flower: One. Pistil length: About 9 mm. Style length: About 2 mm. Style color: Close to 144A. Stigma diameter: About 2 mm. Stigma shape: Rounded, capitate. Stigma color: Close to 144C. Ovary color: Close to 155D. Seeds: About 20 seeds per flower develop.

Pathogen & pest resistance: To date, plants of the new *Erysimum* have not been noted to be resistant to pathogens or pests common to *Erysimum* plants.

Garden performance: Plants of the new *Erysimum* have been observed to have good garden performance and to tolerate temperatures ranging from about −20° C. to about 35° C. and suitable for U.S.D.A. Hardiness Zone 6.

It is claimed:

1. A new and distinct *Erysimum* plant named 'Doerywaci' as illustrated and described.

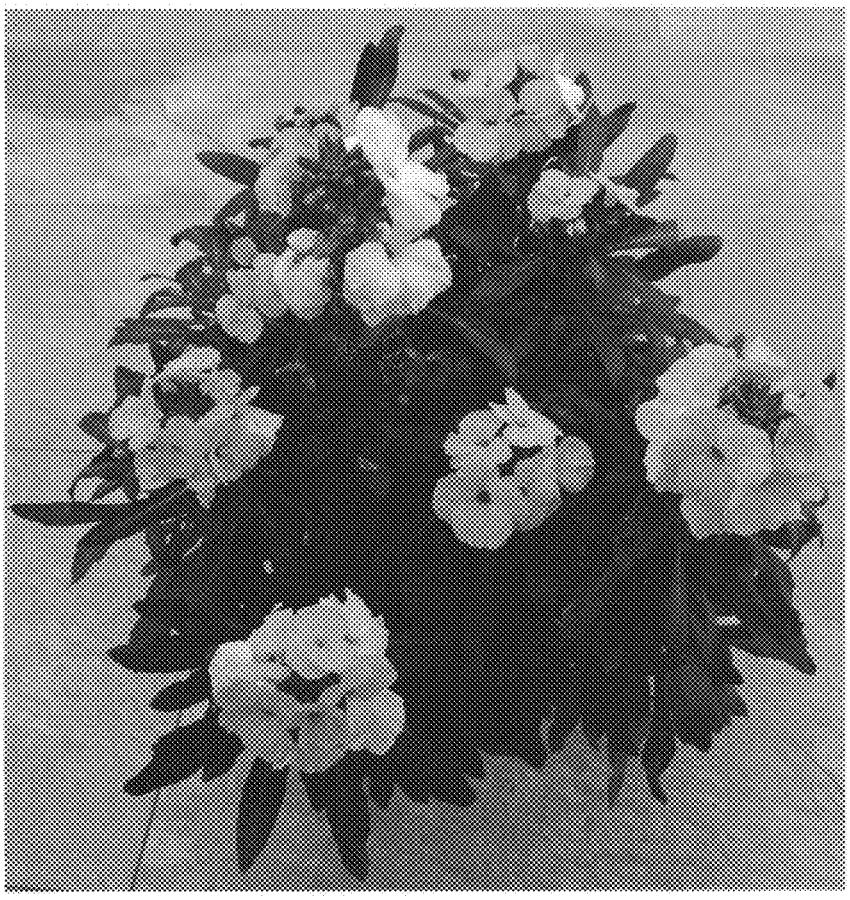

* * * * *